United States Patent [19]

Nakatsuka et al.

[11] 4,079,067
[45] Mar. 14, 1978

[54] METHOD FOR RECOVERING METAL IONS IN AQUEOUS LIQUID

[75] Inventors: Kazunobu Nakatsuka; Katsumi Imada, both of Chiba, Japan

[73] Assignee: Daiichi Seiyaku Co., Ltd., Tokyo, Japan

[21] Appl. No.: 544,608

[22] Filed: Jan. 27, 1975

Related U.S. Application Data

[63] Continuation-in-part of Ser. No. 350,846, Apr. 13, 1973, abandoned.

[51] Int. Cl.$^2$ .............................................. C07D 309/22
[52] U.S. Cl. ................................. 260/345.8 R; 210/21
[58] Field of Search ........................ 210/21; 260/345.8

[56] References Cited

PUBLICATIONS

Chem. Abstracts, vol. 53, 7157h, 1959.
Chem. Abstracts, vol. 57, 12837g, 1962.
Chem. Abstracts, vol. 63, 1458d, 1965.
Chem. Abstracts, vol. 52, 19647f, 1958.
Chem. Abstracts, vol. 68, 8872k, 1968.
Chem. Abstracts, vol. 68, 29149v, 1968.
Chem. Abstracts, vol. 60, 188f, 1964.

*Primary Examiner*—Frank A. Spear, Jr.
*Assistant Examiner*—F. Lander
*Attorney, Agent, or Firm*—Sughrue, Rothwell, Mion, Zinn and Macpeak

[57] ABSTRACT

Esters of comenic acid were found to form metal chelate compounds with various metal ions and these chelate compounds are soluble in organic solvents. This finding makes it possible to recover or remove metal ions from industrial drainage and the like.

11 Claims, No Drawings

METHOD FOR RECOVERING METAL IONS IN AQUEOUS LIQUID metal chelate compounds formed with octyl comenate are shown in Table 1.

Table 1

| chelate compound | solvent benzene | toluene | xylene | 1,2-dichloroethane | methylethylketone | ethyl acetate | chloroform |
|---|---|---|---|---|---|---|---|
| $Fe^{2+}$ | +++ | +++ | +++ | +++ | +++ | +++ | +++ |
| $Sn^{2+}$ | − | − | − | − | + | − | − |
| $Co^{2+}$ | ++ | ++ | ++ | ++ | + | + | ++ |
| $Ni^{2+}$ | ++ | ++ | ++ | ++ | + | ++ | ++ |
| $Cu^{2+}$ | + | + | + | + | + | + | ++ |
| $Zn^{2+}$ | ++ | ++ | ++ | ++ | + | + | ++ |
| $Cd^{2+}$ | ++ | ++ | ++ | + | + | + | ++ |
| $Al^{3+}$ | ++ | ++ | ++ | ++ | ++ | ++ | ++ |
| $Pb^{2+}$ | − | − | − | + | + | + | + |
| $Y^{3+}$ | + | + | + | +++ | + | + | +++ |
| $UO_2^{2+}$ | ++ | ++ | ++ | +++ | + | + | +++ |
| $Sb^{2+}$ | + | + | + | ++ | + | + | ++ |
| $Bi^{2+}$ | + | + | + | ++ | + | + | ++ |
| $Au^{3+}$ | − | − | − | ++ | − | − | ++ |
| $Pt^{2+}$ | + | + | + | + | − | − | + |
| $Cr^{2+}$ | + | + | + | +++ | ++ | ++ | +++ |

+++ : Very soluble (1 g/1 ml or less)
++  : Soluble (1 g/1–10 ml)
+   : Slightly soluble (1 g/10–30 ml)
−   : Very slightly soluble (1 g/100–1000 ml)

CROSS-REFERENCE TO RELATED APPLICATION

This application is a continuation-in-part application of Ser. No. 350,846, KAZUNOBU NAKATSUKA ET AL, filed Apr. 13, 1973, for "METHOD FOR RECOVERING METAL IONS IN AQUEOUS LIQUID", and now abandoned.

This invention relates to a method for recovering and/or removing metal ions from a water solution. Recently, pollution particularly sea or river water pollution by heavy metal ions has constituted one of most important social problems since said pollution may jeoparadize the safety in daily life of citizen. Therefore, a number of counterplans to prevent the pollution have been considered in various parts of country.

As the result of a study to eliminate metal ions in water, the present inventors have found that some comenic esters easily soluble in organic solvents can be effective to this purpose and accomplished the present invention. In the present invention metal cations can be recovered from its aqueous solution as a form of corresponding metal chelate compounds of comenic esters by contacting the aqueous solution at a pH of not less than 3 with comenic esters wherein the alcohol group contains at least 3 carbon atoms dissolved in a hydrophobic organic solvent to transfer the formed chelate compounds to the organic layer.

As for the sorts of comenic esters which can be used in the present invention, the following examples are given; a lower alkyl ester (such as propyl, butyl, isobutyl, amyl, or isoamyl), middle to higher alkyl ester (such as octyl, nonyl, lauryl, or myristyl), an aralkyl ester such as benzyl, and a cycloalkyl ester such as cyclohexyl. Out of them some higher alkyl esters are more preferable for the present purpose.

Any of these esters can easily form a chelate compound together with metal ions (such as Fe, Cu, Cd, Pb, Ni, Co, Zn, Sn, Au, Pt, Al, Sb, Bi, Cr, Y and oxides of uranium group for example $UO_2$) in water and each formed chelate compound is easily soluble in organic solvents. For example, the solubility at 25° C of various Based on these findings the present inventive process is established as follows: firstly, dissolving one of comenic esters mentioned above in a hydrophobic organic solvent, secondly, contacting the organic solution with an aqueous solution containing metal ions by shaking or stirring the two layers to form the corresponding chelate compounds under arranging pH of the aqueous solution with alkali in order to control excessively acidic pH owing to the acid which is formed by a proton released from the comenic ester and a residual anion in the aqueous solution, and then efficiently recovering the metal chelate compounds transferred into the hydrophobic organic layer. Thus, the present method may be utilizable for recovery of noble metals or transuranium elements in a solution as well as for recovery of heavy metals being noxious for the human from the industrial drainage. Moreover it may be applicable to analytical chemistry. Because the formed metal chelate compound produce a specific color (shown in Table 2) which may be colorimetrically measured to determine the amount of the metal.

To remove or recover metal ions from water solution, experiments were made according to the same procedure as in Examples 1 to 5 and various metal chelate compounds were obtained from the organic solvent. The properties of these chelate compounds are shown in Table 3. (With most of the chelates of Table 3, the metals were recovered from the water layer with almost the same recovery ratio as in Examples 1 to 5.) The chelate compounds may have the structure (I) or (II) shown below:

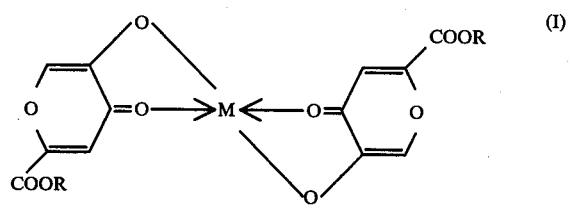

Table 2

| Metal ions | | Comenic esters | | Mole ratio metal: ester | Concentration in water after treatment (%) | Recovery ratio (%) |
|---|---|---|---|---|---|---|
| sort | concentration (%) | sort of alcohol | concentration in CHCl$_3$ | | | |
| Fe$^{2+}$ | 0.224 | amyl | 1.35 | 1:3 | 3.104 × 10$^{-3}$ | 98.61 |
| Fe$^{2+}$ | 0.112 | amyl | 1.35 | 1:6 | 1.111 × 10$^{-3}$ | 98.61 |
| Fe$^{2+}$ | 0.056 | amyl | 1.35 | 1:12 | 0.824 × 10$^{-3}$ | 98.53 |
| Cu$^{2+}$ | 0.198 | octyl | 1.67 | 1:2 | 0.915 × 10$^{-3}$ | 99.79 |
| Pb$^{2+}$ | 0.311 | amyl | 1.35 | 1:2 | 0.5 × 10$^{-3}$ | 99.84 |
| Cd$^{2+}$ | 0.348 | octyl | 1.67 | 1:2 | 7.5 × 10$^{-3}$ | 97.85 |
| Cd$^{2+}$ | 0.02 | lauryl | 1.80 | 1:2 | 0.488 × 10$^{-3}$ | 97.56 |
| Cu$^{2+}$ | 0.02 | lauryl | 1.80 | 1:2 | 0.27 × 10$^{-3}$ | 98.65 |
| Pb$^{2+}$ | 0.02 | lauryl | 1.80 | 1:2 | 0.90 × 10$^{-3}$ | 95.50 |

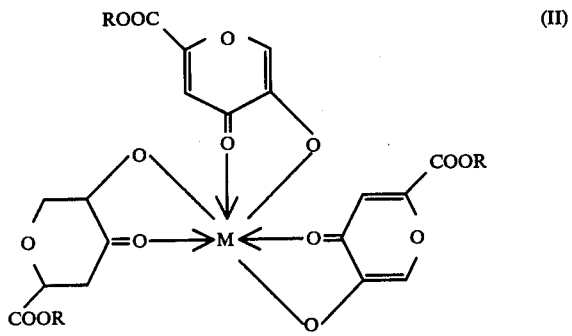

(II)

wherein M represents a divalent metal ion, M' represents a trivalent metal ion and R represents an alkyl or aralkyl group of at least 3 carbon atoms.

Recovery of metal ions themselves from the organic solvent can be achieved by treating the isolated chelate compounds from the organic layer with a mineral acid for example hydrochloric acid under cooling to give as for comenic esters and the metal chloride. As for the organic solvent, use can be made of any solvent which is not soluble in water, for example, benzene, toluene, xylene, chloroform, 1,2-dichloroethane or trichloroethylene. The preferable amount of comenic esters is two to three moles or more per one mole of the metal ions.

In performance of the present process, it is necessary to suitably control the pH of the water solution by addition of alkali so that the water solution may not undergo strong acidification, since the water solution becomes acidic with decrease of metal ions in the water layer. Allowable limit of the pH range varies depending upon the sort of the anions coexisting with the metal ions in the water. For example, in case of a heavy metal salt of a strong acid (e.g. CuSO$_4$) it goes well at a comparatively lower pH, that is, of not less than 3, while in case of a weak anion salt (e.g. CH$_3$COO$^-$) the limit shifts to nearly neutral pH, that is of not less than 4. If the pH goes to acidic beyond these limit, the efficiency of recovery decreases due to opposite proceeding of reaction equilibrium. Generally a range of not less than 3, particularly 4 to 7 is preferable. Alkaline pH may cause precipitation of hydroxides when concentration of the heavy metal ions is considerably high. Therefore, it may be successful even in alkaline pH when concentrations of the cation is not so high.

The performance of the present process is easily operable and possible to remove several ions present in a solution at the same time. Example of efficiency in recovery of metal ions according to the present invention are listed in the following Table 2. If it is necessary or desired to remove cations to a concentration lower than those shown in Table 2, a repetition of the same process or a combination with other processes would be recommendable for the economical performance.

Table 2 shows that metal ions can be efficiently extracted with comenic esters in organic solvents. Quantitative analysis of Fe$^{2+}$ was done according to the colorimetric method using a nitroso R salt (Keiji Yano, The Kagaku no Ryoiki, Extra number 33, Electrophotocolorimetry (1) page 23 Nankodo: Saneo Noda, Biochemistry volume 29, page 199). Other metal ions were quantitatively analyzed according to the atomic absorption analysis method using Atomic Absorption Analizer Type 208 made by Hitachi Seisakusho. (Correspondence of wave lengths and metal ions are as follows: Cu$^{+2}$; 3247 A, Cd$^{+2}$: 2288 A, and Pb$^{+2}$: 2833 A).

The recovery ratios are calculated according to the following equation:

Recovery ratio =

$$\left\{ \frac{\text{concentration of metal ions in water before treatment}}{\text{concentration of metal ions in water before treatment}} - \frac{\text{concentration of metal ions in water after treatment}}{\text{concentration of metal ions in water before treatment}} \right\} \times 100$$

The following examples will explain the present invention in more detail.

EXAMPLE 1

In 200 ml of chloroform was dissolved 3.34 g of octyl comenate. 1.5475 g of copper sulfate (CuSO$_4$·H$_2$O) was dissolved in 200 ml of desalted water (0.0395 g of cupric ion is contained in 20 ml of this solution). Each 20 ml of both solutions was combined and shaken enough. The pH of the aqueous layer was kept at 4.0 with 1% aqueous ammonium solution during the shaking. When the pH became constant without any addition of ammonium, the water layer was separated from the chloroform layer and made to 40 ml of volume with water, in which total cupric ion content was determined to be 0.0183 × 10$^{-2}$g. (Recovery ratio: 99.79%).

EXAMPLE 2

In 200 ml of desalted water was dissolved 1.3 g of cadmium sulfate (CdSO$_4$). 20 ml of this solution (containing 0.06975 g of Cd$^{+2}$ion) was contained and shaken enough with 20 ml of octyl comenate toluene solution whose concentration was same as in Example 1. The pH of the aqueous layer was kept at 4.6. In the same manner as in Example 1 the amount of the $Cd^{+2}$ ion was examined to be 0.0015 g.

EXAMPLE 3

In 200 ml of desalted water was dissolved 1.138 g of lead acetate ($Pb(CH_3COO)_2 3H_2O$). 2.715 g of amyl comenate was dissolved in 200 ml of 1,2-dichloroethane. (0.0622 g of lead ion is contained in 20 ml of this solution.) Each 20 ml of the both solutions was combined and shaken enough. In the same manner as in Example 1 the amount of lead ion was determined to be $0.01 \times 10^{-2}$ g. (recovery ratio: 99.84%).

EXAMPLE 4

In desalted water was dissolved 1.11212 g of ferrous sulfate ($FeSO_4 \cdot 7H_2O$) and made a volume of 100 ml. 2.715 g of amyl comenate was dissolved in 200 ml of trichloroethylene. 20 ml of this solution was each combined with 5 ml ($Fe^{+2}$; 0.011195 g), 10 ml ($Fe^{+2}$; 0.02239 g) and 20 ml ($Fe^{+2}$; 0.04478 g) of the ferrous solution above prepared. In the same manner as in Example 1 each amount of ferrous ions was determined as follows:

| Volume | Amount of the $Fe^{+2}$ | Recovery ratio (%) |
|---|---|---|
| 5 ml | $0.1648 \times 10^{-3}$ | 98.53 |
| 10 ml | $0.222 \times 10^{-3}$ | 98.61 |
| 20 ml | $0.6208 \times 10^{-3}$ | 98.61 |

EXAMPLE 5

In desalted water were dissolved 39.29 mg of cupric sulfate, 18.54 mg of cadmium sulfate and 18.31 mg of lead acetate and made a volume of 50 ml ( in which 10 mg of each metal ion was contained). In 50 ml of chloroform was dissolved 900 mg of lauryl comenate. The both solutions were combined and shaken enough. The pH of the water layer was kept at 3.8 with aqueous ammonia during the shaking. When the pH became constant without any addition of ammonia, the water layer was separated from the chloroform layer and made a volume of 100 ml with water, in which the content of cuppric, cadmium and lead ions were $0.135 \times 10^{-3}$ g (recovery ratio; 98.65%), $0.244 \times 10^{-3}$ g (recovery ratio; 97.56%) and $0.45 \times 10^{-3}$ g (recovery ratio; 95.5%), respectively.

Table 3

| Metal chelate compound | | Melting point | | |
|---|---|---|---|---|
| ester part | metal ion | (° C) | Rational formula | Color |
| octyl | $Fe^{3+}$ | 108 | $(C_{14}H_{19}O_5)_3$ | dark red |
| octyl | $Sn^{2+}$ | 118 | $Sn(C_{14}H_{19}O_5)_2$ | light yellow |
| octyl | $Co^{2+}$ | >245 | $Co(C_{14}H_{19}O_5)_2$ | reddish brown |
| octyl | $Ni^{2+}$ | >223 | $Ni(C_{14}H_{19}O_5)_2$ | yellowish brown |
| octyl | $Cu^{2+}$ | >184 | $Cu(C_{14}H_{19}O_5)_2$ | greenish yellow |
| octyl | $Zn^{2+}$ | >241 | $Zn(C_{14}H_{19}O_5)_2$ | light yellow |
| octyl | $Al^{3+}$ | 112 | $Al(C_{14}H_{19}O_5)_3$ | light yellow |
| octyl | $Cd^{2+}$ | >245 | $Cd(C_{14}H_{19}O_5)_2$ | light yellow |
| octyl | $UO_2^{2+}$ | 179 | $UO_2(C_{14}H_{19}O_5)_2$ | orange |
| octyl | $Y^{3+}$ | >300 | $Y(C_{14}H_{19}O_5)_3$ | light yellow |
| methyl | $Al^{3+}$ | 142 | $Al(C_7H_6O_5)_3$ | colorless |
| methyl | $Ni^{2+}$ | >245 | $Ni(C_7H_6O_5)_2 \cdot 2H_2O$ | yellowish brown |
| methyl | $Zn^{2+}$ | >254 | $Zn(C_7H_6O_5)_2 \cdot 2H_2O$ | yellowish brown |
| butyl | $Cu^{2+}$ | >192 | $Cu(C_{10}H_{11}O_5)_2$ | greenish yellow |
| butyl | $Co^{2+}$ | >300 | $Co(C_{10}H_{11}O_5)_2$ | reddish brown |
| isobutyl | $Cu^{2+}$ | >184 | $Cu(C_{10}H_{11}O_5)_2$ | greenish blue |
| isobutyl | $Co^{2+}$ | >300 | $Co(C_{10}H_{11}O_5)_2$ | reddish brown |
| amyl | $Cu^{2+}$ | >172 | $Cu(C_{11}H_{13}O_5)_2$ | greenish yellow |
| amyl | $Co^{2+}$ | >278 | $Co(C_{11}H_{13}O_5)_2$ | reddish brown |
| isoamyl | $Cu^{2+}$ | >174 | $Cu(C_{11}H_{13}O_5)_2$ | greenish yellow |
| isoamyl | $Co^{2+}$ | >265 | $Co(C_{11}H_{13}O_5)_2$ | reddish brown |
| allyl | $Cu^{2+}$ | >169 | $Cu(C_9H_7O_5)_2$ | greenish yellow |
| allyl | $Co^{2+}$ | >300 | $Co(C_9H_7O_5)_2$ | reddish brown |
| cyclohexyl | $Cu^{2+}$ | >227 | $Cu(C_{12}H_{13}O_5)_2$ | greenish yellow |
| cyclohexyl | $Co^{2+}$ | >260 | $Co(C_{12}H_{13}O_5)_2$ | reddish brown |
| cyclohexyl | $Sb^{2+}$ | 124–127 | $Sb(C_{12}H_{13}O_5)_2$ | light yellow |
| nonyl | $UO_2^{2+}$ | 169–180 | $UO_2(C_{15}H_{21}O_5)_2$ | orange |
| decyl | $Cu^{2+}$ | >193 | $Cu(C_{16}H_{23}O_5)_2$ | greenish yellow |

EXPERIMENT

Experiment 1

Run (1) In 100 ml of water was dissolved 0.406 g of cobalt chloride. 1.15 g of ethyl comenate was dissolved in 100 ml of chloroform. Each solution was combined and shaken sufficiently. In the intersurface between the chloroform layer and the water layer, the formation of powdery crystals of the cobalt chelate compound of ethyl comenate was observed. The crystals were filtered and dried to yield 0.6 g (46.1%) of the cobalt chelate compound of ethyl comenate. The pH of the water layer was kept at 6.0 using 1% aqueous ammonium solution during the shaking.

The cobaltic ion content in the water layer of the solution from which the crystals were removed was measured using an atomic absorption spectrophotomer. As a result, it was confirmed that 24.7% of cobaltic ion based on the original cupric ion content remained.

Further, the chloroform layer was condensed and dried to yield 0.38 g (29.2%) of the chelate compound.

Runs (2)-(9) The above run (1) was conducted except for using various alkyl comenates and metal compounds as shown in the table below.

The results obtained are shown in Table 4 below.

residual content of cupric ion in the water layer was measured.

The results obtained are shown in Table 6 below.

TABLE 6

| pH of Water Layer | Cupric Ion Extraction Ratio From Water Layer (%) |
| --- | --- |
| 2.1 | 16.7 |
| 3.0 | 53.7 |
| 4.0 | 81.9 |
| 4.5 | 89.4 |
| 5.0 | 99.8 |

While the invention has been described in detail and

TABLE 4

| Run No. | Alkyl of Alkyl Comenate | Amount of Alkyl Comenate (ml) | Amount of Chloroform (ml) | Metal Compd. | Amount of Metal Compd. (g) | Amount of Water (ml) | Residual Metal Content in Water Layer (%) | Weight of Crystals Formed (g) | Yield of Chelate Compd. (g) |
| --- | --- | --- | --- | --- | --- | --- | --- | --- | --- |
| 1 | $C_2H_5$ | 1.15 | 100 | $CoCl_2$ | 0.406 | 100 | 24.7 | 0.6 (46.1%) | 0.38 (29.2%) |
| 2 | $C_3H_7$ | 1.24 | " | " | " | " | 10.0 | Non | 1.27 (90.0%) |
| 3 | $C_8H_{17}$ | 1.68 | " | " | " | " | 1.0 | " | 1.84 (99.0%) |
| 4 | $C_2H_5$ | 1.15 | " | $Ni(CH_3COO)_2 \cdot 4H_2O$ | 0.78 | " | 21.0 | 0.98 (75.3%) | 0.05 (3.7%) |
| 5 | $C_3H_7$ | 1.24 | " | " | " | " | 8.0 | Non | 1.30 (92.0%) |
| 6 | $C_8H_{17}$ | 1.68 | " | " | " | " | 0.8 | " | 1.84 (99.2%) |
| 7 | $C_2H_5$ | 1.15 | " | $CuSo_4 \cdot 5H_2O$ | 0.78 | " | 25.0 | " | 1.00 (75.0%) |
| 8 | $C_3H_7$ | 1.24 | " | " | " | " | 4.7 | " | 1.37 (95.3%) |
| 9 | $C_8H_{17}$ | 1.68 | " | " | " | " | 0.2 | " | 1.87 (99.8%) |

Experiment 2

The solubility of various cobalt chelate compounds formed from various alkyl comenates in various hydrophobic organic solvents saturated with water at 25° C was measured using an atomic absorption spectrophotomer.

The results obtained are shown in Table 5 below.

TABLE 5

| Chelate Compound | Solvent | | | | | | |
| --- | --- | --- | --- | --- | --- | --- | --- |
| | Benzene | Toluene | Xylene | 1,2-dichloroethylene | Methyl Ethyl Ketone | Octyl Acetate | Chloroform |
| Methyl Comenate-Co | − | − | − | − | − | − | − |
| Ethyl Comenate-Co | − | − | − | − | − | − | − |
| Propyl Comenate-Co | ++ | ++ | ++ | ++ | + | + | ++ |
| Octyl Comenate-Co | ++ | ++ | ++ | ++ | + | + | ++ |

++ : Soluble (1 g/1–10ml)
+ : Slightly soluble (1 g/10–30 ml)
− : Very slightly soluble (1 g/100–1000 ml)

Experiment 3

1.5475 g of copper solfate was dissolved into 200 ml of water to prepare a aqueous solution of a pH of 4.4. 3.34 g of octyl comenate was dissolved in 200 ml of chloroform. 20 ml portion of each solution was combined and sufficiently shaken. The pH of the water layer was 2.1. The water layer was separated from the chloroform layer, and the cupric ion content in the water layer was measured using.

The above experiment was conducted except for adjusting the pH of the water layer to 3.0, 4.0, 4.5 and 5.0 with a 1% aqueous ammonium solution, and the with reference to specific embodiments thereof, it will be apparent to one skilled in the art that various changes and modifications can be made therein without departing from the spirit and scope thereof.

What is claimed is:

1. A method for recovering metal ions in aqueous liquid which comprises maintaining the pH of the aqueous liquid at not less than 3 and contacting said aqueous liquid containing metal ions with an effective recovering amount of a comenic ester wherein the alcohol group contains at least 3 carbon atoms in a hydrophobic solvent.

2. A method of claim 1, wherein the metal ion is a member selected from the group consisting of Fe, Cu, Cd, Pb, Ni, Co, Zn, Au, Pt, Al, Sb, Bi, Sn, Cr, Y and $UO_2$.

3. A method of claim 1, wherein the comenic ester is a member selected from the group consisting of a lower alkyl, middle alkyl, higher alkyl, aralkyl and cycloalkyl ester of comenic acid.

4. A method of claim 1, wherein the hydrophobic solvent is a member selected from the group consisting of benzene, toluene, xylene, chloroform, 1,2-dichloroethane, and trichloroethylene.

5. A method of claim 1, wherein the pH is from 4 to 7.

6. A method for recovering metal ions in aqueous liquid which comprises contacting a comenic ester wherein the alcohol group contains at least 3 carbon atoms and said ester is selected from the group consisting of a lower alkyl, middle alkyl, higher alkyl, aralkyl and cycloalkyl ester of comenic acid dissolved in a hydrophobic solvent selected from the group consisting of benzene, toluene, xylene, chloroform, dichloroethane and trichloroethylene with the aqueous liquid containing metal ions, with the pH of the aqueous layer being maintained at not less than three.

7. A method of claim 6, wherein the comenic ester is a $C_5$–$C_8$ aliphatic hydrocarbon ester and the solvent is 1,2-dichloroethane and the pH is four to seven.

8. A method of claim 6, wherein the comenic ester is amyl ester and the solvent is 1,2-dichloroethane and the pH is four to seven.

9. A method of claim 7, wherein the comenic ester is octyl ester and the solvent is 1,2-dichloroethane and the pH is four.

10. The method of claim 1, wherein the alcohol group of said comenic ester is propyl, butyl, isobutyl, amyl, isoamyl, octyl, nonyl, lauryl, myristyl, benzyl or cyclohexyl.

11. The method of claim 6, wherein the alcohol group of said comenic ester is propyl, butyl, isobutyl, amyl, isoamyl, octyl, nonyl, lauryl, myristyl, benzyl or cyclohexyl.

* * * * *